United States Patent
Sioshansi et al.

(10) Patent No.: US 6,419,621 B1
(45) Date of Patent: *Jul. 16, 2002

(54) COILED BRACHYTHERAPY DEVICE

(75) Inventors: Piran Sioshansi, Lincoln; Raymond J. Bricault, West Boylston, both of MA (US)

(73) Assignee: RadioMed Corporation, Tyngsborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,769

(22) Filed: May 21, 1999

Related U.S. Application Data

(63) Continuation-in-part of application No. 09/046,744, filed on Mar. 24, 1998, which is a continuation-in-part of application No. 08/956,863, filed on Oct. 24, 1997, now Pat. No. 6,030,333.

(51) Int. Cl.$^7$ ................................................. A61N 5/00
(52) U.S. Cl. .......................................................... 600/3
(58) Field of Search .......................................... 600/1–8

(56) References Cited

U.S. PATENT DOCUMENTS

| | | |
|---|---|---|
| 4,702,228 A | 10/1987 | Russell, Jr. et al. |
| 4,754,745 A | 7/1988 | Horowitz |
| 4,946,435 A | 8/1990 | Suthanthiran et al. |

(List continued on next page.)

FOREIGN PATENT DOCUMENTS

| | | |
|---|---|---|
| RU | 799 189 | 8/1983 |
| WO | 99/33063 | 7/1999 |

OTHER PUBLICATIONS

Blasko, "Long–Term Outcomes Of External Beam Irradiation And 1–25/:Pd–103 Brachytherapy Boost For Prostate Cancer", *I. J. Radiation Oncology•Biology•Physics*, vol. 36, No. 1, Supplemental, Dec. 1996.

Dattoli et al., "$^{103}$Pd Brachytherapy and External Beam Irradiation For Clinically Localized, High–Risk Prostatic Carcinoma", *Int. J. Radiation Oncology Biol. Phys.*, vol. 35, No. 5, pp. 875–879, Dec. 1996.

Finger et al., "Palladium 103 Ophthalmic Plaque Radiotherapy", *Arch Ophthalmol*, vol. 109, pp. 1610–1613, Dec. 1991.

Finger et al., "Palladium–103 Versus Iodine–125 For Ophthalmic Plaque Radiotherapy", *Int. J. Radiation Oncology Biol. Phys.*, vol. 27, No. 4, pp. 849–854, Dec. 1993.

Fix, PD–103 Seeds Treat Intraocular Tumors With Less Radiation Exposure To Healthy Tissue, *Advance For Administrators in Radiology*, p. 47, Sep. 1994.

Guttman, "Interstitial Brachytherapy Making Comeback", *Urology Times*, Oct. 1993.

(List continued on next page.)

*Primary Examiner*—Samuel G. Gilbert
(74) *Attorney, Agent, or Firm*—McDermott, Will & Emery

(57) ABSTRACT

A brachytherapy device in the form of a radioactive coiled wire. The wire used to form the coil is typically between about 10 and 200 micrometers in diameter, and the coil formed from the wire has an outer diameter of between about 25 micrometers and about 1000 micrometers. The coil can be formed first from a wire and then made radioactive. Alternatively, the wire can be made radioactive first and then formed into a coil. Methods of incorporating a radioisotope into the wire or coil include, for example, nuclear transformation and ion implantation, which do not affect the flexibility and other mechanical properties of the coil. Thin radioisotope films can also be applied to the wire.

16 Claims, 1 Drawing Sheet

U.S. PATENT DOCUMENTS

| | | | |
|---|---|---|---|
| 4,957,476 A | | 9/1990 | Cano |
| 5,030,195 A | | 7/1991 | Nardi |
| 5,059,166 A | | 10/1991 | Fischell et al. |
| 5,163,896 A | * | 11/1992 | Suthanthiran et al. ......... 600/8 |
| 5,176,617 A | | 1/1993 | Fischell et al. |
| 5,342,283 A | | 8/1994 | Good |
| 5,405,309 A | | 4/1995 | Carden, Jr. |
| 5,411,466 A | | 5/1995 | Hess |
| 5,498,227 A | | 3/1996 | Mawad |
| 5,503,614 A | | 4/1996 | Liprie |
| 5,575,749 A | | 11/1996 | Liprie |
| 5,607,442 A | | 3/1997 | Fischell et al. |
| 5,624,372 A | | 4/1997 | Liprie |
| 5,637,073 A | | 6/1997 | Freire |
| 5,722,984 A | | 3/1998 | Fischell et al. |
| 5,924,974 A | * | 7/1999 | Loffler ............................ 600/3 |
| 5,997,463 A | * | 12/1999 | Cutrer ............................ 600/8 |
| 6,024,690 A | * | 2/2000 | Lee et al. ....................... 600/3 |
| 6,030,333 A | * | 2/2000 | Sioshansi et al. .............. 600/3 |

OTHER PUBLICATIONS

Prestidge et al., "Post–Treatment Biopsy Results Following Interstitial Brachytherapy In Early Stage Prostate Cancer", 37th Annual Scientific Meeting of the American Society For Therapeutic Radiology and Oncology, Miami Beach, Florida, Oct. 9, 1995.

Ragde, "Brachytherapy (Seed Implantation) for Clinically Localized Prostate Cancer", *J. Surg. Oncol.*, vol. 64, pp. 79–81, Dec. 1997.

Ragde et al., "Brachytherapy In The Management Of Clinically Organ–Confined Prostate Cancer", First International Consultation on Prostate Cancer, World Health Organization, Monacao, Jun. 20–22, pp. 1–12, 1996.

Skerrett, "Radioactive Pellets Speed Prostate Recovery", *Medical World News*, Jan. 1994.

Skolnick, "Radiation Therapy For "Wet" Type Molecular Degeneration Shows Promise In Early Trials", *JAMA*, vol. 277(9) Dec. 1997.

"Therapeutic Options Available For Treating Prostate Cancer", *The BBI Newsletter*, vol. 19, No. 4, pp. 72–74, Apr. 1996.

"TheraSeed™ Palladium 103 Implants", *Theragents Corporation*, May 31, 1990.

"Beta Radiation May Stop Wet Macular Degeneration ", *eyesotopes*, The International Newsletter For Eye Tumor Experts, No. 5, Apr. 1997.

Eigler et al., "$A^{48}$ Vanadium Brachytherapy Source for Treatment of Coronary Artery Restenosis", *Vascular Brachytherapy*, Chapter 23, pp. 231–236, Dec. 1996.

International Search Report for PCT/US00/08948, Jul. 2000.

* cited by examiner

COILED BRACHYTHERAPY DEVICE

CROSS-REFERENCE TO RELATED APPLICATION

This application is a continuation-in-part of copending U.S. application Ser. No. 09/046,744, filed on Mar. 24, 1998, and of copending U.S. application Ser. No. 08/956,863, filed on Oct. 24, 1997 now U.S. Pat. No. 6,030,333, both of which are assigned to the assignee of the present invention and are hereby incorporated by reference into this application.

TECHNICAL FIELD

The invention is directed to implantable brachytherapy devices.

BACKGROUND OF THE INVENTION

It is known to treat proliferative tissue, such as tumors, lesions and stenoses of biological passageways, with radiation in order to inhibit or prevent cellular proliferation by preventing replication and migration of cells and by inducing programmed cell death. Traditional high-dose external beam radiation treatment, and prolonged low dose rate, close-distance radiation treatment (brachytherapy), are well-established therapies for the treatment of cancer, a malignant form of cellular proliferation.

It is important in the administration of radiation that it be properly targeted so as to be effective against undesirable cellular proliferation without adversely affecting normal cellular responses. Externally applied radiation requires careful control over the depth and breadth of radiation penetration so as not to damage healthy tissue surrounding the lesion to be treated. Close-distance radiation treatment also requires careful control over the penetration and directionality of the radiation, but this can be done over substantially smaller distances.

The radioactivity may be incorporated into or onto an implantable device. Such implantable devices are typically quite expensive to manufacture. In particular, if radioactivity is added to the device, the device may only be effective for brachytherapy during a relatively short period during which the radioactivity is provided at a useful (therapeutic) level. Depending on the radioisotope used, the decay time may be as short as hours, days or weeks.

The current state of the art brachytherapy for treatment of localized lesions such as tumors of, for example, the prostate, breast, brain, eye, liver, or spleen, employs radioactive, sealed source seeds. The term "sealed source", as used herein, means that radioisotopes incorporated into a device are integral with the device and cannot be dislodged or released from the host material of the device in the environment of usage. A typical sealed source seed includes a radiation source encapsulated within an impermeable, biocompatible capsule made of, for example, titanium, which is designed to prevent any leaching or release of the radioisotope. The seeds are approximately the size of a grain of rice (typically 0.81 mm in diameter by 4.5 mm long) and are implanted individually at a treatment site within and/or around a lesion, typically with a medium bore (18-gauge) delivery needle.

Disadvantages of the use of such seeds as brachytherapy devices include their nature as discrete, or point, sources of radiation, and the corresponding discrete nature of the dosages which they provide. In order to provide an effective radiation dose over an elongated or wide target area, the seeds should be uniformly and relatively closely spaced. The need to ensure accurate and precise placement of numerous individual radiation sources undesirably prolongs the surgical procedure, and hence the exposure of the surgical team to radiation. Moreover, the use of discrete seeds requires an elaborate grid matrix for their proper placement. This requirement is labor-intensive, and therefore costly. In addition, the discrete nature of the seeds renders them more susceptible to migration from their intended locations, thereby subjecting portions of the lesion, the treatment site, and surrounding healthy tissue to over- or under-dosage, reducing the effectiveness and reliability of the therapy.

Other disadvantages exist in radioactive seed therapy. Relatively few radionuclides are suitable for use in sealed-source seeds, because of limited availability of radioisotopes with the necessary combination of half-life, specific activity, penetration depth and activity, and geometry. In addition, the implantation of seeds generally requires a delivery needle with a sufficiently large bore to accommodate the seeds and may, in some cases, require an additional tubular delivery device. The use of a relatively large delivery needle during seeding may cause unnecessary trauma to the patient and displacement of the lesion during the procedure. Also, because of the risk of migration or dislodgement of the seeds, there is the risk that healthy tissues near or remote from the lesion site will be exposed to radiation from seeds which have become dislodged from their intended locations and possibly carried from the body within urine or other fluids.

Various radioisotopes have been proposed for brachytherapy. Brachytherapy devices made of palladium-103 are desirable because palladium-103 has a half life of about 17 days and a photon energy of 20.1–23 KeV, which makes it particularly suitable for use in the treatment of localized lesions of the breast, prostate, liver, spleen, lung and other organs and tissues.

Because palladium-103 is unstable and not naturally occurring in the environment, it must be manufactured, generally either by neutron activation of a palladium-102 target, or by proton activation of a rhodium target. These processes are disclosed in, for example, U.S. Pat. No. 4,702,228 to Russell, Jr. et al. (neutron activation) and U.S. Pat. No. 5,405,309 to Carden, Jr. (proton activation).

Brachytherapy devices employing radioisotope coatings are also known. U.S. Pat. No. 5,342,283 to Good discloses the formation of concentric radioactive and other discrete coatings on a substrate by various deposition processes, including ion plating and sputter deposition processes, as well as via exposure of an isotope precursor, such as palladium-102, to neutron flux in a nuclear reactor.

A disadvantage of the radioactive devices made by any of the above processes is that they cannot be made economically or simply. The processes are either prohibitively expensive and require lengthy and costly wet chemistry separation steps to isolate the radioactive isotope from the non-radioactive precursor, or they are relatively complicated, multistep processes which are difficult to control and which may produce coatings that can deteriorate with time and/or exposure to bodily fluids, resulting in dissemination of radioactive and other materials into the body, with potentially harmful consequences.

A highly versatile form of a device for interstitial radiation treatment is a wire or rod which can be inserted into the tissue at a lesion site and then bent or shaped as needed to encircle or otherwise assume a useful shape for administration of radiation to the lesion and/or to surrounding tissue. Greater versatility, flexibility and specificity of treatment can be provided as the size (diameter) of the wire decreases; however, such fine wires are also generally difficult to see, handle and maneuver, and this limits their utility in many treatment applications.

U.S. Pat. No. 5,498,227 to Mawad discloses a shielded implantable radioactive wire which includes a radioactive inner core and a buffer or shielding layer in the form of a flexible metal wire or ribbon wrapped around the core. The purpose of the buffer layer is to attenuate radiation emitted from the inner core. The wire can be formed into a helical coil shape and can be made of a shape-memory material which allows the device to be inserted into a treatment site in a straightened configuration and then relaxed to its original helical shape. The device has particular application as an expandable helical coil stent to deliver therapeutic radiation to, and maintain the patency of, occluded biological passageways. The diameter of the inner core, as well as of the wire used as the buffer layer, is in the range of about ten to fifty thousandths of an inch (0.010"–0.050"), or about 0.25 to 1.25 millimeter, and the diameter of the helical coil formed from the wire is in the range of about 1 millimeter to 2 centimeters.

U.S. Pat. Nos. 5,176,617 and 5,722,984 to Fischell et al. also disclose radioactive helical coil stents for use in maintaining the patency of biological passageways. Such stents generally have an undeployed diameter in the range of about 1.5 to 2 millimeters, and a deployed diameter in the range of about 2 to 4 millimeters.

A problem with the Mawad and Fischell et al. devices is that they are generally characterized by a stiffness and rigidity which, although beneficial in maintaining the patency of a lumen or passageway, are not optimum for use in many applications in which extra-luminal brachytherapy, such as, for example, interstitial brachytherapy, is needed.

It would therefore be an advancement in the art to provide a highly versatile, highly flexible, general purpose brachytherapy device for use primarily in interstitial applications which can also be relatively easily and economically fabricated.

SUMMARY OF THE INVENTION

According to one aspect of the invention, there is provided an implantable brachytherapy device comprising a radioactive coiled wire. The diameter of the wire for almost all applications is between about 10 and about 200 micrometers, and the outer diameter of the coil is between about 25 and about 1000 micrometers (1 millimeter). In this range the wire is very thin and may be difficult to handle and see with the naked eye and, when in the body, difficult to detect using x-ray and ultrasound imaging techniques. By coiling the wire the device is easier to handle and to see, both with the naked eye and when in the body under x-ray or ultrasound. Further, in one application, the brachytherapy device is sufficiently adaptable so that when it is positioned in proximity to a lesion, the device can shrink and/or change it shape as the lesion shrinks and/or changes shape. The device is thus highly useful in interstitial brachytherapy applications.

The radioactive coiled wire preferably includes one or more radioisotopes which have been incorporated into the wire so that the wire comprises a substantially unitary material. The term "substantially unitary material", as used herein, refers to a radioisotope-containing material which retains virtually all of the properties (mechanical, chemical, electrical, optical, etc.) of the host material prior to incorporation of the radioisotope. More specifically, when a substantially unitary material includes a radioisotope, there is no distinguishable interface between the host material and the radioisotope.

In one preferred embodiment, the wire is made substantially of a transmutable material which can be converted to a radioactive material upon exposure of the wire to an accelerated beam of charged particles having a predetermined energy. The charged particles can be protons, deuterons or alpha particles. In one preferred embodiment, the transmutable material comprises rhodium and the radioactive material comprises palladium-103. In another preferred embodiment, the transmutable material comprises tantalum and the radioactive material comprises tungsten-181. In other embodiments, the transmutable material can comprise, for example, stainless steel, which includes iron, carbon and various alloying agents such as chromium, cobalt, vanadium, titanium, tantalum, tungsten, and nickel, and minor amounts of other elements such as manganese and arsenic. The radioactive material will comprise one or more of various radioisotopes of these alloying elements.

According to another embodiment, ion implantation techniques can be used to incorporate the radioisotope into the wire so that the wire comprises a substantially unitary material.

According to still another embodiment, the wire includes one or more radioisotopes which have been applied onto the wire as a thin film so that the wire comprises a substantially "near-unitary" material. A "near-unitary" material, as the term is used herein, is defined as a material which retains substantially all of the mechanical properties of the wire, or host material, prior to application of the radioisotope. The radioisotope is applied as a thin film onto the wire and is not integrated into the material of the wire.

The device of the invention is preferably adapted for either substantially permanent or temporary implantation into a patient and may include anchoring structures at points along its length or at its ends for securing the device in tissue.

The intensity of the radioactivity of the wire, prior to its formation into a coil, is a function of the location and type of radioisotope(s) in or on it. The intensity of the radioactivity of the coil is a function of not only these parameters, but also of the shape, size, turns density and pitch angle of the coil. The coiled wire preferably has an aspect ratio (ratio of coil length to coil diameter) of at least 3 to 1. The pitch angle can vary from essentially zero degrees, so that the wire is essentially linear, to ninety degrees, so that the coil is so tightly wound that it essentially defines a tubular structure.

In a preferred embodiment, the diameter of the wire is about 50 micrometers and the outer diameter of the coil formed from the wire is about 350 micrometers.

According to another aspect of the invention, there is provided a method of making an implantable coiled brachytherapy device. The method comprises the steps of providing a flexible wire of a non-radioactive material, incorporating one or more radioisotopes into at least a portion of the wire so that the wire comprises a substantially unitary material, and forming the wire into a coil having a preselected shape, size, turns density, pitch angle and sufficient flexibility such that the coil can change shape in response to changes in surrounding tissue. Such changes could include, for example, changes in the shape, size, location and/or contour of the lesion and/or the surrounding tissue.

In an alternate embodiment, the method comprises the steps of providing a flexible wire of a non-radioactive material, forming the wire into a coil having a preselected shape, size, turns density, pitch angle, and sufficient flexibility such that the coil can change shape in response to changes in surrounding tissue, and incorporating one or more radioisotopes into at least a portion of the wire so that the wire comprises a substantially unitary material.

In a preferred embodiment, the wire or coil can be made radioactive by nuclear transformation or ion implantation techniques so as to create a substantially unitary material.

According to another aspect of the invention, there is provided a method of making an implantable coiled brachytherapy device. The method comprises the steps of providing a flexible wire of a non-radioactive material, applying a thin film containing one or more radioisotopes onto at least a portion of the wire so that the wire comprises a substantially near-unitary material, and forming the wire into a coil having a preselected shape, size, turns density and pitch angle.

In an alternate embodiment, the method comprises the steps of providing a flexible wire of a non-radioactive material, forming the wire into a coil having a preselected shape, size, turns density and pitch angle, and applying a thin film containing one or more radioisotopes onto at least a portion of the wire so that the wire comprises a substantially near-unitary material.

In a preferred embodiment, the total thickness of the film is not greater than about 1 percent of the outer diameter of the coil.

According to still another aspect of the invention, there is provided a method of making an implantable coiled brachytherapy device. The method comprises the steps of providing a flexible wire of a non-radioactive material having a diameter of between about 10 and about 200 micrometers, incorporating one or more radioisotopes into at least a portion of the wire so that the wire comprises a substantially unitary material, and forming the wire into a coil having an outer diameter of between about 25 and about 1000 micrometers and having a preselected shape, turns density and pitch angle.

In an alternate embodiment, the method comprises the steps of providing a flexible wire of a non-radioactive material having a diameter of between about 10 and about 200 micrometers, forming the wire into a coil having an outer diameter of between about 25 and about 1000 micrometers and having a preselected shape, turns density and pitch angle, and incorporating one or more radioisotopes into at least a portion of the wire so that the wire comprises a substantially unitary material.

According to still another aspect of the invention, a method of making an implantable coiled brachytherapy device comprises the steps of providing a flexible wire of a non-radioactive material having a diameter of between about 10 and about 200 micrometers, applying a thin film containing one or more radioisotopes onto at least a portion of the wire so that the wire comprises a substantially near-unitary material, and forming the wire into a coil having an outer diameter of between about 25 and about 1000 micrometers and having a preselected shape, turns density and pitch angle.

In an alternate embodiment, the method comprises the steps of providing a flexible wire of a non-radioactive material having a diameter of between about 10 and about 200 micrometers, forming the wire into a coil having an outer diameter of between about 25 and about 1000 micrometers and having a preselected shape, turns density and pitch angle, and applying a thin film containing one or more radioisotopes onto at least a portion of the wire so that the wire comprises a substantially near-unitary material.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

The foregoing and other features and advantages of this invention will be better understood from the following detailed description taken with the accompanying drawings, in which.

DETAILED DESCRIPTION OF THE DRAWINGS

The invention is directed to a coiled brachytherapy wire which is of a size that is particularly useful in interstitial brachytherapy applications. The wire is very thin and may be difficult to handle and see with the naked eye. When positioned in the body, the wire may be difficult to see in an x-ray or ultrasound image.

A significant advantage provided by the coiled form of the device is a greatly improved visibility and maneuverability of the device. A very fine wire that is coiled is much easier to see and handle than a very fine wire which is not coiled. By coiling the wire, superior flexibility, pushability and kink resistance are obtained, and the coil can be shaped to suit any treatment application. In particular, a flexible coiled wire in proximity to a lesion has the ability to shrink and/or change shape as the lesion shrinks and/or changes shape. This feature allows the coiled brachytherapy device of the invention to be used in numerous treatment applications and potentially long-term therapies. Moreover, as the diameter of the wire decreases, the advantages of coiling are even more apparent. Additional advantages will be made apparent hereinafter.

Figures 1A, 1B, 1C:
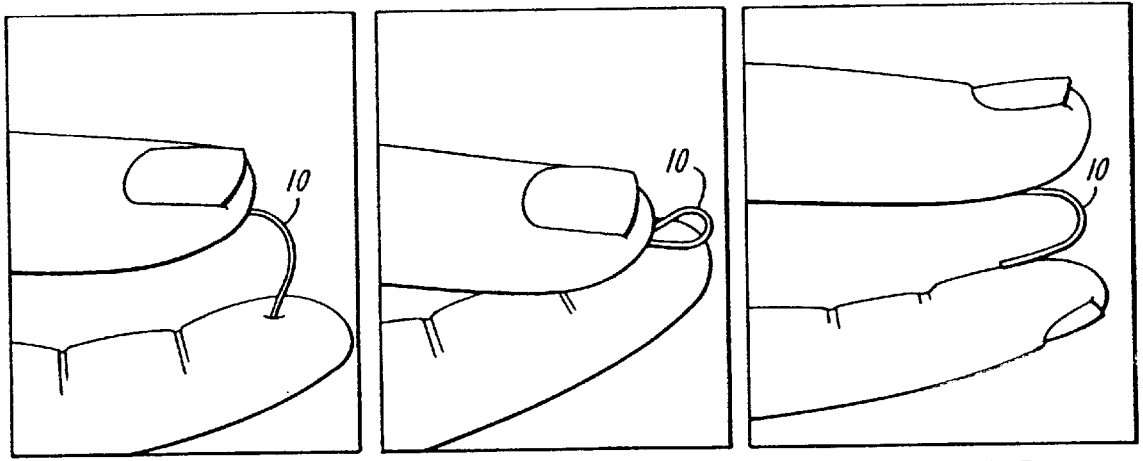
FIGS. 1A–1C are perspective views of a coiled brachytherapy device according to the invention.

A flexible wire coil 10 according to the invention is generally biased to return to its original shape and size if stretched or bent, as shown in FIGS. 1A–1C. The coiled brachytherapy wire of the invention is significantly smaller in diameter and significantly more flexible than a helical coil stent. A helical stent is designed to maintain the patency of a vessel, duct or other biological passageway, which is typically at least 2 mm in diameter, by expanding against the walls of the passageway once installed. In contrast, the coiled brachytherapy device of the invention is designed to penetrate and surround lesions which are embedded in tissue, without necessarily offering significant structural support or rigidity to the surrounding tissue. The coiled brachytherapy device of the invention is primarily for use in interstitial brachytherapy applications. It is much smaller in diameter than most biological passageways in which a stent is used, and it is highly flexible, in contrast to a stent, which is relatively rigid.

The coiled wire can be fabricated from a substantially non-radioactive material and then converted into a radioactive material, such as via nuclear transmutation from exposure to a high-energy beam of charged particles, ion implantation of a radioisotope, or by some other method of incorporation of a radiation source into the material of the device. The coil can be formed and then made radioactive, and therefore it can be easily and economically worked, handled, transported and stored in a non-radioactive state. Alternatively, a wire can be made radioactive and then formed into a coil just prior to its use in a particular application.

Uniformly radioactive wires and coils emit radiation in a generally cylindrical pattern extending about their central axes; however, a coiled wire defines an interior volume and therefore also can emit radiation towards a central axis within the interior volume. The tubular structure defined by a coiled wire has particular advantages in brachytherapy applications. For example, a radioactive tube or coil exhibits minimal self-attenuation of the radioactivity, as there is no core of material through which radioactivity must pass and dissipate. As the wire diameter decreases, the effective wall thickness of a tube defined by the coiled wire approaches zero, and the release of a unit of radiation per unit of solid volume becomes more efficient.

In one preferred embodiment, a relatively low dosage of a radioisotope can be incorporated into a wire using nuclear transmutation technology, and the wire then coiled to produce a brachytherapy device having a relatively high level of radioactive intensity. In particular, an accelerated beam of charged particles having a relatively low localized power density can be used to convert a wire made from a transmutable material into a radioactive material, and the wire can then be coiled to form a high intensity brachytherapy device. A very high-power activating beam (on the order of, for example, 12 MeV at 2 mA) can be spread over a relatively large area or over a large number of wires, thereby reducing the localized power density on any single wire. Many individual small, high-intensity brachytherapy devices can be formed by coiling the radioactive wires.

The intensity of the radioactivity of the coiled brachytherapy device of the present invention is a function of the species and location of radioisotope(s) on the device, as well as the shape, size, turns density and pitch angle of the coiled wire.

The cross-section of the wire, as well as of the coil, can have any shape which is convenient to manufacture consistent with the particular application. The most common cross-sectional shapes for the wire and for the coil are circular and oblong. Regular and irregular multi-faceted or multi-sided cross-sectional shapes may also be feasible in certain applications.

The size of the coil refers to its maximum outer dimension or diameter. The flexibility of the coil is determined by the outer dimension of the coil and by other factors, including the properties of material selected for the coil. In general, the ratio of coil diameter or outer dimension to wire diameter or outer dimension ranges from about 2.5:1 to about 40:1. A preferred ratio of coil diameter to wire diameter is about 7:1. As an example, in a preferred embodiment a wire having a diameter of about 50 micrometers can be formed advantageously into a coil having an outer diameter of about 350 micrometers. Regardless of its diameter, however, the coiled device of the invention provides superior flexibility, pushability, kink resistance, visibility and ease of handling.

Figure 2A:
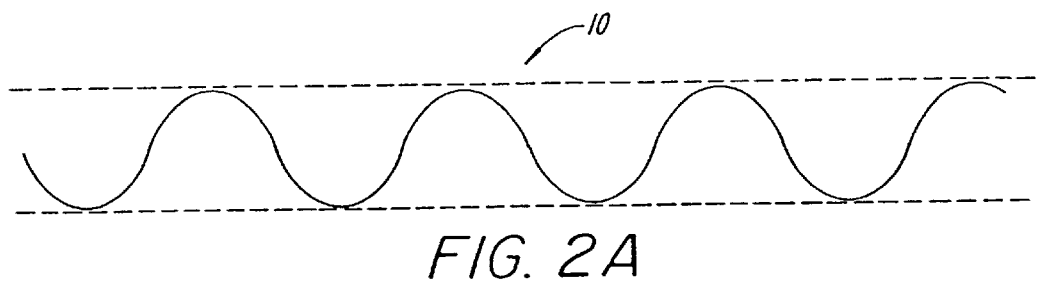
FIG. 2A is a simplified diagram of a coiled brachytherapy device having a pitch angle which approaches zero.
Figure 2B:
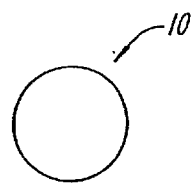
FIG. 2B is an end view of the device of FIG. 2A.
Figure 3:
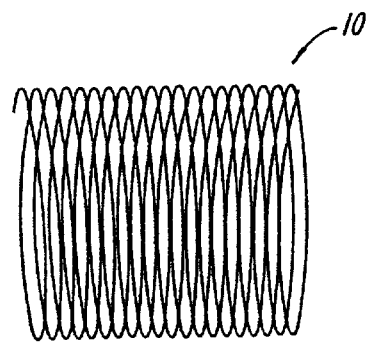
FIG. 3 is a simplified diagram of a coiled brachytherapy device having a pitch angle of about 90°.

The turns density and pitch angle of the coil also affect its radiation intensity. A less densely coiled structure with a pitch angle that approaches zero will have the properties of a long, gently spiraled wire, as illustrated in FIG. 2A. A more densely coiled structure with a pitch angle of essentially ninety degrees will have the properties of a tightly wound coil and simulate a tubular structure, as illustrated in FIG. 3.

In one preferred embodiment, the coiled brachytherapy wire is made at least partially of a transmutable material which can be transmuted into a radioisotope-containing material by subjecting the wire to an accelerated beam of charged particles of a predetermined energy. The transmutation process is effected in a nuclear accelerator or cyclotron and is highly efficient if a beam of sufficiently high-energy particles is used.

The transmutable material is preferably rhodium, which is transmutable into radioactive palladium-103 upon exposure to an accelerated beam containing protons, deuterons or alpha particles. Another preferred material is tantalum, which is transmutable to radioactive tungsten-181 upon exposure to an accelerated proton beam.

Transmutable materials other than rhodium can be used. In particular, alloys containing more than one transmutable element can be employed, and the transmutable elements can be converted to various radioisotopes. Such alloys, when subject to activating beams of accelerated particles, do not typically transmute to a single radioactive species. For example, stainless steel containing, for example, iron, carbon, and various alloying elements such as chromium, cobalt, vanadium, titanium, manganese, and/or nickel, as well as other impurities such as arsenic, phosphorus and manganese, can be transmuted to a material which includes radioisotopes of iron, cobalt, vanadium, titanium, chromium, and manganese.

In particular, iron-56 can be transmuted to cobalt-56 in a proton, neutron (p, n) activation reaction. The half-life of cobalt-56, a beta and gamma emitter, is approximately 77.3 days. Alternatively, iron-56 can be transmuted to cobalt-57 in a deuteron, neutron (d, n) activation reaction. The half-life of cobalt-57, a gamma emitter, is approximately 270 days. Still another reaction involves the transmutation of iron-56 to cobalt-58 in an alpha, proton, neutron ($\alpha$, p, n) reaction. The half-life of cobalt-58, also a beta and gamma emitter, is approximately 71.3 days.

Chromium-53 and chromium-54 can be transmuted to manganese-54 in deuteron, neutron (d, n) and proton, neutron (p, n) reactions, respectively. Manganese-54 is a gamma emitter and has a half-life of approximately 303 days.

Titanium-48 may be transmuted to vanadium-48 in a proton, neutron (p, n) reaction. Vanadium-48 is a beta and gamma emitter and has a half-life of approximately 16 days.

Tantalum-181 can be transmuted to tungsten-181 in a proton, neutron (p, n) reaction. Tungsten-181 is a gamma emitter and has a half-life of approximately 140 days.

In addition, nickel-titanium alloys, such as those used in guidewires, can also undergo nuclear transmutation to provide a radioactive species which may be suitable for brachytherapy applications.

Alternatively, a substantially unitary material can be created by incorporating the radioisotope into the material of the wire or coil by ion implantation, In the ion implantation process, a filament in thermionic emission (with associated confinement) is used in an ion source to create a plasma. The positive ions produced in the plasma are extracted and accelerated in the presence of an electric field. A magnetic mass separator is used to select one particular isotope of an elemental species and deliver it to the work station, in which multiple devices to be treated are mounted. Finally, by using an electromagnetic focusing lens and raster scanning plates, the ion beam is focused and scanned onto the material to be made radioactive. The energetic ions impinge on the surface of the host material and physically penetrate it. The velocity of the implanted species is slowed by electronic and nuclear collision with the host surface atoms, and the implanted ions eventually come to a stop as they become embedded in the host material. At the final rest position, the implanted species form chemical or physical bonds to the host atoms. Examples of chemical bonds include the formation of nitrides and carbides, while examples of physical bonds include the formation of alloys, which can be either ordered or amorphous. In either case, the incoming ion becomes an integral part of the host material, creating a substantially unitary, sealed source material. Extensive research has borne out the mechanical and chemical stability of the ion implanted species in rather demanding tribological and corrosive environments.

The ion implantation technology used in the present invention provides for the incorporation of a known amount of a radioisotope into the wire or coil at a predetermined density so as to provide a predetermined dose of radiation in a predetermined delivery pattern.

In the coiled brachytherapy device of the present invention, it is important that the flexibility of the coil be maintained and preserved, regardless of the method in which the coil is formed or of the method in which the radioisotope is incorporated into or onto the material of the coil. The radioactive coiled wire preferably also comprises a substantially sealed source so that no radioisotopes can be separated or leached from the wire or coil in use.

Alternate methods of rendering the wire or coil radioactive involve the incorporation of a radioisotope onto the wire or coil as a thin film so as to create a "near-unitary" material, which is defined herein as a host material having a radioisotope-containing thin film coating which has an aggregate film thickness of less than about 1 percent of the maximum outer dimension of the coil. The radioisotope thin film or films which meet this criterion do not have any substantial effect on the flexibility or other mechanical properties of the coil.

Other processes for incorporating radioisotopes onto the device of the invention include, for example, ion beam assisted deposition, sputter coating, ion plating, evaporation, cathodic arc deposition and other derivative physical vapor deposition methods, laser ablation and plating.

The brachytherapy device of the invention can be further treated with a substantially radiation-transparent, biocompatible encapsulant over at least a portion of its surface. The purpose of the encapsulant is to provide an additional barrier coating or sealant to prevent leaching of any residual radioactivity from the device after transmutation. The encapsulant coating may be applied to all or a portion of the device, before or after it is made radioactive, and before or after the wire is formed into a coil, and may comprise, for example, a polymer, metal, nonmetal, or ceramic. Typical techniques for applying the encapsulant include, for example, plating, sputtering, evaporation deposition, ion plating, plasma spray deposition, flame spray deposition, and chemical vapor deposition. Typical coating thicknesses may range from about 50 Angstroms to about 250 micrometers.

A brachytherapy kit for delivering a predetermined dose of radiation to a disease site or lesion within a patient may include, for example, a brachytherapy device in the form of a coiled wire as described herein, and a delivery vehicle, such as a syringe, catheter or the like, for inserting the elongated element into the patient at or near the treatment site. The brachytherapy device is provided in a form which is suitable for the particular application, such as treatment of prostate tumors.

Unlike the prior art radioactive seeds, which are a composite of pellets of radioactive material encased in a non-radioactive titanium shell, the brachytherapy devices of the present invention can be made into radioactive seed-like structures made directly from, for example, rhodium wires which have been made radioactive and then cut to the desired seed dimensions just prior to implantation. Alternatively, the rhodium wires can be cut to desired lengths and the rhodium seed-like structures thus formed stored in a non-radioactive state for later conversion to a radioactive material. In still another embodiment, radioactive coils can be cut into desired lengths to form seed-like brachytherapy structures. In still another embodiment, a radioisotope can be incorporated into wires, which are then cut to the desired length. With any of these methods, many costly fabrication steps are avoided in the manufacture of radioactive seeds using the radioisotope incorporation techniques disclosed herein.

The use of radioactive wires and, now, coils for the treatment of proliferative tissue is an advancement over the current seeding techniques. The radiation dosage obtainable using radioactive wires and coils can be either substantially uniform or variable over the entire length of the wire. In any event, the dosage can be discriminately applied based upon the specific therapy requirements by tailoring the shape of the device and the radiation pattern emitted from it. In addition, the wires or coils can be positioned accurately and reliably, without risk that the radiation source will migrate become dislodged from its intended position.

The device of the invention can be permanently or temporarily implanted in the patient. It can also be removed from the patient after brachytherapy treatment has been completed, restored to a radioactive state, and reimplanted to deliver radiation in another application.

The device can include one or more anchoring structures of various forms known in the art for fixation of the device in the host tissue so that it remains in place after implantation for the duration of the radiation treatment, and possibly indefinitely.

The coiled form of the device is primarily intended to enhance the flexibility and maneuverability of a fine radioactive wire so that its use in interstitial and other brachytherapy applications is practical and feasible. Unlike a helical coiled stent, the coiled wire of the invention is not intended to provide significant structural support for mechanical or biological structures and is significantly smaller in diameter than typical stents. To be suitable for any interstitial brachytherapy application, the coiled brachytherapy device of the invention should preferably be as compliant to the host tissue as possible. As hoop strength or rigidity of the coil of the invention increases, the likelihood of potential complications arising from use of the device also increases.

One application in which the brachytherapy device of the present invention is of particular interest is the treatment of prostate tumors, both benign and malignant. Other applications which may also be suitable for treatment with the device of the present invention include the treatment of breast, spleen, liver, lung and brain tumors, as well as other localized tumors.

For the treatment of, for example, tumors of the prostate, it is preferred to employ a coiled rhodium wire which is transmutable to palladium-103 upon irradiation with protons, deuterons or alpha particles at an energy level of at least 4 MeV. Palladium-103 is already used in radioactive seeds used to treat prostate tumors, and thus its behavior in, and suitability for, this application is well-documented.

Selective masking and/or activation of portions of a device, as well as different coiling techniques, can produce devices which emit radiation in a characteristic pattern which is not solely determined by the shape of the device. For example, a selectively activated rhodium wire may produce either a constant-radius radiation pattern or a variable-radius radiation pattern along its length. Similarly, a uniformly coiled wire will produce a substantially uniform radiation pattern, whereas a non-uniformly coiled wire will produce a nonuniform radiation pattern.

Although a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. An implantable brachytherapy device, consisting essentially of a radioactive coiled wire, wherein the diameter of the wire is between about 10 and about 200 micrometers, and wherein the outer diameter of the coil is between about 25 micrometers and about 1000 micrometers.

2. An implantable brachytherapy device according to claim 1, wherein the radioactive coiled wire includes one or more radioisotopes which have been incorporated into the wire so that the wire consists essentially of a substantially unitary material.

3. An implantable brachytherapy device according to claim 2, wherein the wire is made substantially of a transmutable material which is convertible to a radioactive material upon exposure of the wire to an accelerated beam of charged particles having a predetermined energy.

4. An implantable brachytherapy device according to claim 3, wherein the charged particles are selected from the group consisting of protons, deuterons and alpha particles.

5. An implantable brachytherapy device according to claim 4, wherein the transmutable material comprises rhodium and the radioactive material comprises palladium-103.

6. An implantable brachytherapy device according to claim 1, wherein the coiled wire is characterized by a pitch angle which ranges from approximately 0° to approximately 90°.

7. An implantable brachytherapy device according to claim 1, wherein the intensity of the radiation from the coiled wire is a function of the shape, size, turns density and pitch angle of the coiled wire.

8. An implantable brachytherapy device according to claim 1, wherein the diameter of the wire is about 50 micrometers and the outer diameter of the coil is about 350 micrometers.

9. An implantable brachytherapy device, comprising a radioactive coiled wire, wherein the diameter of the wire is between about 10 and about 200 micrometers, wherein the outer diameter of the coil is between about 25 micrometers and about 1000 micrometers, wherein the radioactive coiled wire includes one or more radioisotopes which have been incorporated into the wire so that the wire comprises a substantially unitary material, wherein the wire is made substantially of a transmutable material which is convertible to a radioactive material upon exposure of the wire to an accelerated beam of charged particles having a predetermined energy, wherein the charged particles are selected from the group consisting of protons, deuterons and alpha particles, and wherein the transmutable material comprises tantalum and the radioactive material comprises tungsten-181.

10. An implantable brachytherapy device according to claim 1, wherein the radioactive coiled wire includes one or more radioisotopes which have been applied onto the wire as a thin film so that the wire comprises a substantially near-unitary material, wherein the total thickness of the film on the wire is not more than about 1 percent of the outer diameter of the coil.

11. An implantable brachytherapy device, consisting essentially of a radioactive coiled wire, wherein the diameter of the wire is between about 10 and about 200 micrometers, wherein the outer diameter of the coil is between about 25 micrometers and about 1000 micrometers, wherein the radioactive coiled wire includes one or more radioisotopes which have been incorporated into the wire so that the wire comprises a substantially unitary material, wherein the wire is made substantially of a transmutable material which is convertible to a radioactive material upon exposure of the wire to an accelerated beam of charged particles having a predetermined energy, wherein the charged particles are selected from the group consisting of protons, deuterons and alpha particles, and wherein the transmutable material comprises rhodium and the radioactive material comprises palladium-103.

12. An implantable brachytherapy device, consisting essentially of a radioactive coiled wire, wherein the diameter of the wire is between about 10 and about 200 micrometers, and wherein the outer diameter of the coil is at least about 25 micrometers and less than about 1000 micrometers.

13. An implantable brachytherapy device, consisting essentially of a radioactive coiled wire, wherein the diameter of the wire is between about 10 and about 200 micrometers, and wherein the outer diameter of the coil is between about 25 micrometers and about 900 micrometers.

14. An implantable brachytherapy device, consisting essentially of a radioactive coiled wire, wherein x-rays emitted from the wire are characterized by a photon energy of between about 20.1 and about 23 keV.

15. An implantable brachytherapy device, consisting essentially of a radioactive coiled wire, wherein the diameter of the wire is between about 10 and about 200 micrometers, wherein the outer diameter of the coil is between about 25 micrometers and about 1000 micrometers, wherein the wire is made of rhodium and is activated by a beam of charged particles to produce palladium-103 x-rays having a photon energy of between about 20.1 and about 23 keV.

16. An implantable brachytherapy device, consisting essentially of a radioactive coiled wire, wherein the diameter of the wire is about 50 micrometers and the outer diameter of the coil is about 350 micrometers.

* * * * *